United States Patent
Hope et al.

(10) Patent No.: US 9,265,795 B2
(45) Date of Patent: Feb. 23, 2016

(54) CELLULAR COMPOSITIONS FOR USE IN THERAPY

(75) Inventors: Andrew Hope, Guildford (GB); Erik Miljan, Guildford (GB); John Sinden, Guildford (GB)

(73) Assignee: RENEURON LIMITED (GB)

( * ) Notice: Subject to any disclaimer, the term of this patent is extended or adjusted under 35 U.S.C. 154(b) by 236 days.

(21) Appl. No.: 13/132,475

(22) PCT Filed: Dec. 7, 2009

(86) PCT No.: PCT/GB2009/051659
§ 371 (c)(1),
(2), (4) Date: Sep. 20, 2011

(87) PCT Pub. No.: WO2010/064054
PCT Pub. Date: Jun. 10, 2010

(65) Prior Publication Data
US 2012/0076854 A1    Mar. 29, 2012

(30) Foreign Application Priority Data
Dec. 5, 2008 (GB) .................................. 0822246.5

(51) Int. Cl.
A61K 35/12 (2015.01)
A61K 9/48 (2006.01)
A61K 35/28 (2015.01)
A61K 9/19 (2006.01)
A61K 38/06 (2006.01)
A61L 27/38 (2006.01)

(52) U.S. Cl.
CPC . *A61K 35/28* (2013.01); *A61K 9/19* (2013.01); *A61K 38/063* (2013.01); *A61L 27/3834* (2013.01); *A61K 35/12* (2013.01); *A61K 2035/128* (2013.01)

(58) Field of Classification Search
CPC ....... A61K 9/19; A61K 38/063; A61K 35/12; A61K 2035/128; A61K 35/28; A61L 27/3834
See application file for complete search history.

(56) References Cited

U.S. PATENT DOCUMENTS

| | | | |
|---|---|---|---|
| 6,328,960 B1 * | 12/2001 | McIntosh et al. | 424/93.71 |
| 6,399,384 B1 | 6/2002 | Jat | |
| 6,465,215 B1 | 10/2002 | Price et al. | |
| 6,498,018 B1 * | 12/2002 | Carpenter | 435/29 |
| 6,569,421 B2 | 5/2003 | Hodges | |
| 6,852,533 B1 | 2/2005 | Rafii et al. | |
| 7,048,921 B2 | 5/2006 | Sinden et al. | |
| 7,247,298 B2 | 7/2007 | Hodges | |
| 7,371,374 B2 | 5/2008 | Sinden et al. | |
| 7,416,888 B2 | 8/2008 | Sinden et al. | |
| 7,419,827 B2 | 9/2008 | Sinden et al. | |
| 7,666,672 B2 | 2/2010 | Sinden et al. | |
| 8,932,577 B2 | 1/2015 | Sinden et al. | |
| 2003/0207450 A1 * | 11/2003 | Young et al. | 435/368 |
| 2005/0069527 A1 | 3/2005 | Laughlin et al. | |
| 2005/0142659 A1 | 6/2005 | Rafii et al. | |
| 2006/0067918 A1 | 3/2006 | Sinden et al. | |
| 2007/0042339 A1 | 2/2007 | Toner et al. | |
| 2007/0048726 A1 | 3/2007 | Baust et al. | |
| 2012/0093786 A1 | 4/2012 | Sinden et al. | |
| 2014/0341868 A1 | 11/2014 | Sinden et al. | |

FOREIGN PATENT DOCUMENTS

| | | |
|---|---|---|
| EP | 1 645 626 A1 | 4/2006 |
| WO | WO 99/11758 A2 | 3/1999 |
| WO | WO 00/02572 A1 | 1/2000 |
| WO | WO 00/18414 A1 | 4/2000 |
| WO | WO 03/059276 A2 | 7/2003 |
| WO | WO 2004/009766 A2 | 1/2004 |
| WO | WO 2006/055685 A2 | 5/2006 |
| WO | WO 2006/125991 A1 | 11/2006 |
| WO | WO 2006/130433 A2 | 12/2006 |
| WO | WO 2007/013771 A1 | 2/2007 |
| WO | WO 2007/032634 A1 | 3/2007 |
| WO | WO 2008102118 A1 * | 8/2008 |
| WO | WO 2008152640 A2 * | 12/2008 |
| WO | WO 2009/020201 A1 | 2/2009 |
| WO | WO 2009/120996 A1 | 10/2009 |
| WO | WO 2010/089605 A1 | 8/2010 |

OTHER PUBLICATIONS

Syme et al., Biology of Blood and Marrow Transplantation, 10: 135-141, 2004.*
Baust et al., In Vitro Cell. Dev. Biol.—Animal, 36: 262-270, 2000.*
Rowley et al., Cytotherapy et al., 1(6): 439-446, 1999.*
Richards et al., Stem Cells, 22: 779-789, 2004.*
Newman et al., Biomaterials, 5763-5771, 2004.*
Baust, J.M. "Advances in Media for Cryopreservation and Hypothermic Storage" *BioProcess International*, Jun. 2005, Supp:46-56.
Costa, P.F., etal., "Cryopreservation of Cell/Scaffold Tissue-Engineered Constructs," *Tissue Engineering: Part C*, 2012, vol. 18, No. 11, pp. 852-858.

(Continued)

*Primary Examiner* — Thaian N Ton
(74) *Attorney, Agent, or Firm* — Saliwanchick, Lloyd & Eisenschenk

(57) ABSTRACT

The present invention provides a therapeutic composition comprising:
(i) Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine, glutathione; and
(ii) stem cells or progenitor cells,
wherein the composition does not comprise a dipolar aprotic solvent, in particular DMSO.

The present invention also relates to methods of formulating said composition for cryopreservation and subsequent direct administration to a patient, and medicaments comprising said composition.

16 Claims, 5 Drawing Sheets

(56) References Cited

OTHER PUBLICATIONS

Xu, X., et al., "Effects of cryopreservation on human mesenchymal stem cells attached to different substrates," *Journal of Tissue Engineering and Regenerative Medicine*, 2014, vol. 8, pp. 664-672.

Alessandri, G. et al. "Genetically Engineered Stem Cell Therapy for Tissue Regeneration" *Ann. N.Y. Acad. Sci.*, 2004, 1015:271-284.

Ford, M.C. et al. "A macroporous hydrogel for the coculture of neural progenitor and endothelial cells to form functional vascular networks in vivo" *PNAS*, Feb. 2006, 103(8):2512-2517.

Gray, B.H. et al. "Atherosclerotic Peripheral Vascular Disease Symposium II Lower-Extremity Revascularization: State of the Art" *Circulation*, Dec. 2008, 118:2864-2872.

Katare, R. et al. "Injection of human neural stem cell line in a mouse hind limb ischemia model promotes muscle neovascularisation" *AHA Scientific Sessions*, Nov. 2009, 2 pages.

Katare, R. et al. "Injection of a human neural stem cell line promotes muscle neovascularisation in a diabetic hind limb ischemia mouse model" *UK Diabetes: Annual Professional Conference*, Mar. 2010, 1 page.

Keller, L.H. "Bone Marrow-Derived Aldehyde Dehydrogenase-Bright Stem and Progenitor Cells for Ischemic Repair" *Spotlight on Heart Failure Translational Research*, 2009, 15:202-206.

Madeddu, P. et al. "Injection of hNSC line in a mouse hindlimb ischemia model promotes muscle neovascularisation" *AHA Scientific Sessions*, Nov. 2009, 1 page.

Nolden, L. et al. "Humane embryonale Stammzellen" *Bundesgesundheitsbl-Gesundheitsforsch-Gesundheitsschutz*, 2008, 51:1026-1032.

Pollock, K. et al. "A conditionally immortal clonal stem cell line from human cortical neuroepithelium for the treatment of ischemic stroke" *Experimental Neurology*, 2006, 199:143-155.

Sprengers, R.W. et al. "Progenitor Cell Therapy in Patients With Critical Limb Ischemia Without Surgical Options" *Ann. Surg.*, Mar. 2008, 247(3):411-420.

Office Action dated Mar. 24, 2015, issued in U.S. Appl. No. 14/450,733.

\* cited by examiner

CELLULAR COMPOSITIONS FOR USE IN THERAPY

CROSS-REFERENCE TO RELATED APPLICATION

This application is the U.S. national stage application of International Patent Application No. PCT/GB2009/051659, filed Dec. 7, 2009, the disclosure of which is hereby incorporated by reference in its entirety, including any figures, tables, or drawings.

FIELD OF THE INVENTION

The present invention relates to cell therapy compositions and the methods of formulating such compositions.

BACKGROUND OF THE INVENTION

The development of cell therapies is the focus of investigations for the treatment of numerous indications with currently unmet needs. Such therapies administered as a cell suspension ideally require the use of a vehicle that is compatible with the cells, non-toxic to the recipient, and suitable for storage of the therapy for a sufficient time prior to and during administration.

Preservation of cell therapies in ambient or hypothermic (2° C. to 8° C.) conditions is necessary for early phase clinical trials of allogeneic therapies. It is also more likely to be used for autologous cell therapies, which utilize patients' own cells as a starting material.

Cryopreservation is likely to be necessary for long-term storage of cell therapies prior to administration. Later phase multi-centre trials will require substantially longer storage times than can be achieved using hypothermic storage, as the therapeutic cell product is likely to be manufactured centrally and distributed over a number of months. Ultimately, post-authorisation manufacture of cell therapy products will necessitate storage for numerous years.

The use of the cryoprotectant dimethylsulfoxide (DMSO) has great utility in preserving cells in liquid nitrogen freezers (~-195° C.). DMSO is a member of the class of dipolar aprotic solvents, which also includes dimethylformamide, N-methyl-2-pyrrolidone and hexamethylphosphoramide, and is the most common cryoprotectant used in the manufacture and banking of cell therapies. However, this solvent is toxic to the cell product and subsequently to the treated patient (Hubel, 2001; Sauer-Heilborn et al., 2004). For example, in bone marrow transplants, almost all patients receiving DMSO-cryopreserved cells suffer side effects and a small number experience serious complications. Direct effects during infusion and delayed-onset side effects have been observed in a dose dependent manner. The effects described occurred when the cell formulation was administered systemically and so any formulation ingredients are diluted and widely distributed. In contrast, administration via direct injection into tissue (for example, intracranial, intramuscular or intracardiac administration) would increase local toxicity effects. Methods to remove the DMSO content from cryopreserved cells have reduced DMSO-related complications and side-effects (Syme et al., 2004). However, these processes were inefficient with as little as 60% of the cell product recovered (Calmels et al., 2003).

The use of glycerol and trehalose has been shown to be effective in the storage of cryopreserved sperm (Storey et al., 1998), however this method has been found to be ineffective with different cell types.

Previous formulations of cells for administration have relied on cell culture medium and modified saline solutions. Although these formulations are suitable for administration, they do not preserve the viability of the cell product for more than a few hours. This precludes them from clinical studies, wherein the time taken to release the product for clinical administration, followed by transit, and the potentially lengthy process of implantation (up to 9 hours in total) may render the cells non-viable. Therefore there is necessity to increase the shelf-life of these products beyond this 9 hour period in order to overcome the immediate obstacles of early clinical trials. In addition, in order for a cell therapy product to be commercially viable, a much longer storage strategy is needed.

The excipient HypoThermosol®-FRS (HTS-FRS) (BioLife Solutions, Inc) is a hypothermic storage solution that was initially developed as a perfusate to be used during cardiac arrest coupled with profound hypothermia, in order to minimise ischemic injury. HTS-FRS is a commercially-available formulation designed to mediate the level of post-storage necrosis and apoptosis in cells undergoing prolonged periods of hypothermic (2° C.-10° C.) preservation.

U.S. Pat. No. 6,921,633 discloses a method of preserving a cell, tissue or organ by contacting said cell, tissue or organ with a hypothermic storage solution comprising a composition that inhibits apoptosis and a sufficient concentration of vitrification composition to vitrify said solution.

U.S. Pat. No. 6,632,666 discloses a gel-based composition for use in the nanothermic, hypothermic or cryopreservative storage and transport of cell samples comprising HTS-FRS and a gelling agent.

WO2005/009766 discloses a pharmaceutical composition comprising liver cells, HTS and DMSO which can be stored at cryothermic temperatures.

Following storage of these compositions at hypothermic or cryothermic temperatures, substantial processing of the cell therapy product is required in order to remove the toxic cryoprotectants prior to administration. This may lead to additional release testing which is both burdensome and costly.

Therefore, there is a need for compositions and formulations which provide an alternative to DMSO and which can be stored at cryothermic temperatures and used as a vehicle for direct administration of cell therapies.

SUMMARY OF THE INVENTION

According to a first aspect, the present invention provides a composition for use in therapy, wherein the composition comprises:
  (i) Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine, glutathione; and
  (ii) stem cells or progenitor cells,
and wherein the composition does not comprise a dipolar aprotic solvent, in particular DMSO.

According to a second aspect of the invention, a method of formulating stem cells or progenitor cells for administration to a patient comprises suspending the cells in a composition according the first aspect of the invention. The method may further comprise the following initial steps:
  (a) suspending the cells in a composition according to the first aspect of the invention;
  (b) storing the cell suspension of step (a) at a cryothermic temperature; and
  (c) thawing the suspension of step (b).

The cell suspension may also be stored at a hypothermic temperature after step (b) or step (c), i.e. the suspension can be transferred from a cryothermic temperature to a hypothermic temperature.

According to a third aspect of the invention, a medicament in a unit dose form comprises the composition according to the first aspect of the invention.

DETAILED DESCRIPTION OF THE DRAWINGS

The present invention is described with reference to the accompanying drawings wherein.

Figure 9:
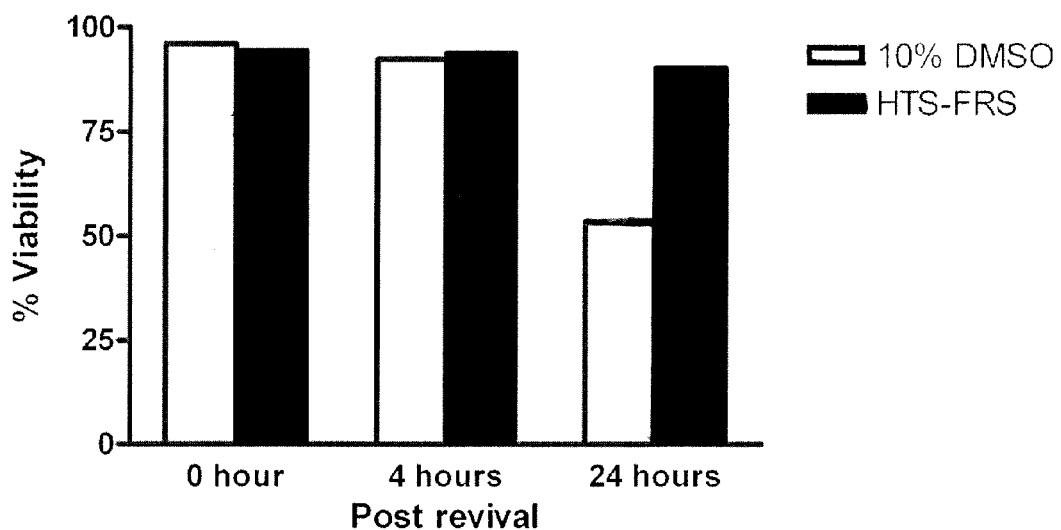
Figure 10:
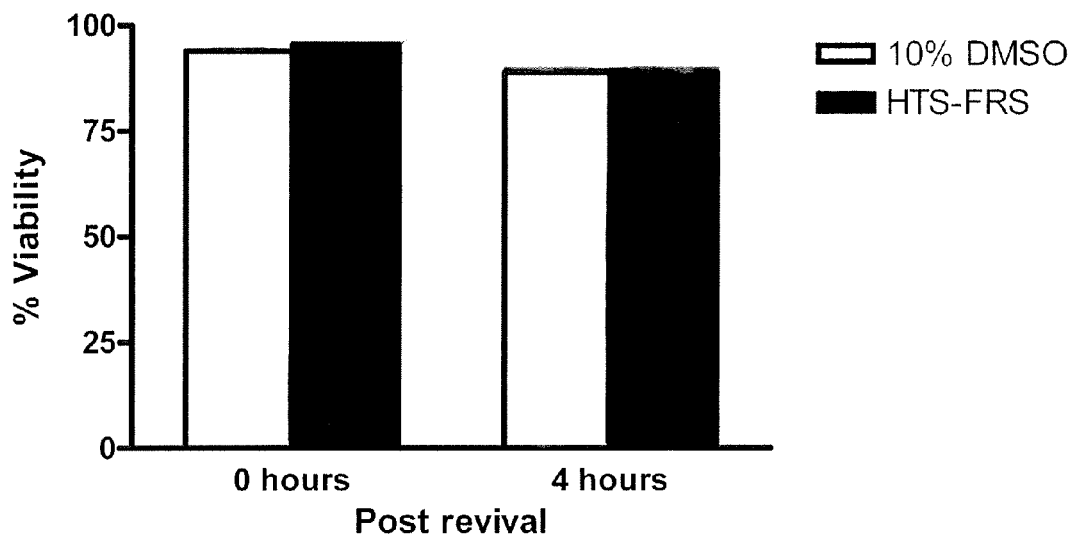

FIG. 9 is a graph showing the viability of exemplar retinal stem cells immediately upon thawing and 4 hours and 24 hours post-thaw at ambient temperature, wherein cells were cryopreserved for one month in liquid nitrogen vapour in media containing either 10% DMSO or HTS-FRS; and FIG. 10 is a graph showing the viability of exemplar mesenchymal stem cells immediately upon thawing and 4 hours post-thaw at ambient temperature, wherein cells were cryopreserved for one month in liquid nitrogen vapour in media containing either 10% DMSO or HTS-FRS.

DETAILED DESCRIPTION OF THE INVENTION

The present invention relates to cell compositions and methods of formulating cell compositions suitable for preservation at cryothermic temperatures, wherein the preserved cell compositions can be administered directly to a patient following thawing.

As used herein, the term 'patient' refers to a mammal including a non-primate (e.g. a cow, pig, horse, dog, cat, rat and mouse) and a primate (e.g. a monkey and human), and preferably a human.

The present invention provides compositions suitable for therapeutic use comprising stem cells and progenitor cells suspended in a hypothermic storage solution which comprises Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine and glutathione and does not contain DMSO (dimethyl sulfoxide, $(CH_3)_2SO$) or any other dipolar aprotic solvents. The hypothermic storage solution is available commercially under the trade names HypoThermosol®, or HypoThermosol®-FRS (HTS-FRS) and is manufactured by BioLife Solutions, Inc. The composition of the invention is suitable for storage at cryothermic temperatures and, following thawing, can be administered directly to a patient in need of the cells of the composition without requiring further processing or testing.

The class of dipolar aprotic solvents that are excluded from the composition of the present invention includes DMSO, dimethylformamide, N-methyl-2-pyrrolidone and hexamethylphosphoramide. Members of this class are highly polar organic solvents that dissolve polar and non-polar compounds. These solvents are miscible in a wide range of organic solvents as well as water and have relatively high boiling points. These solvents are excluded from the composition of the invention because they are toxic to the cell product and subsequently to the treated patient.

The present invention also provides a method for formulating stem cells or progenitor cells for clinical administration by suspending said cells in the storage solution HTS-FRS. The method of the invention is based upon the surprising finding that cells suspended in HTS-FRS in the absence of DMSO, or other dipolar aprotic solvents, can be preserved at cryothermic temperatures and subsequently administered directly to a patient. Cells formulated for clinical administration in accordance with the present invention may be recovered from a cell culture system. Alternatively, cryopreserved cells may be recovered from storage. Accordingly, in an embodiment of the invention, prior to suspending the cells in HTS-FRS for direct administration to a patient, the following initial steps are carried out:

(a) cells are suspended in HTS-FRS;
(b) the suspended cells of step (a) are stored at a cryothermic temperature; and
(c) the suspended cells of step (b) are thawed.

Following cryopreservation (step (b)) or thawing (step (c)) the cell suspension may also be stored at a hypothermic temperature.

As used herein, the term "hypothermic temperature" refers to temperatures within the range 2° C. to 8° C.

As used herein, the term "cryothermic temperatures" refers to temperatures below −20° C., preferably within the range −70° C. to −200° C., and most preferably within the range −80° C. to −196° C. The term "cryopreservation" refers to the storage of cells at a temperature within these ranges.

As used herein, the term "ambient temperature" refers to temperatures within the range 15° C. to 25° C.

The present invention also provides a medicament in unit dose form, comprising stem cells or progenitor cells suspended in HTS-FRS. The medicament is suitable for direct administration to a patient in need thereof, via any suitable delivery means, and preferably via implantation into the tissue or systemic delivery.

The cells utilised in the invention are stem cells or progenitor cells. Preferably, the cells are human somatic stem cells or human progenitor cells, and most preferably selected from human haematopoietic stem cells, human mesenchymal stem cells, human neural stem cells (neuroepithelial cells) and human retinal progenitor cells.

The cells are present in the composition of the invention at a concentration in the range of 20,000 to 80,000 cells/µl, preferably 40,000 to 60,000 cells/µl.

The cell compositions, formulations and medicaments according to the present invention are suitable for clinical administration via direct tissue implantation or systemic administration, including intraperitoneal, intravenous, intraarterial and intramuscular administration. The cell formulation may be administered via any suitable method, however administration via a cell delivery cannula is preferred.

The stem or progenitor cells of the composition of the invention may be comprised in biocompatible scaffolds or microcarriers. The association of cells with scaffolds or microcarriers may promote better cell survival with needle injection and, following transplantation, better integration into host tissue. The scaffolds or microcarriers are preferably biodegradable polymeric substances, most preferably poly (D,L lactic-co-glycolic acid) (PLGA), which is described by Bible et al (2009). Alternatively, the scaffolds or micro-carriers may be smooth, macroporous or microporous structures comprising substances including poly-L-lactide (PLLA), collagen, fibronectin, glycosaminoglycans (GAGs), fibrin, starch, cellulose arabinogalactan (larch gum), alginic acid, agar, carrageenan, chitin, hyaluronic aid, dextran, gellan gum, pullulan, hydroxyapatite, polyhydroxyalkanoates (PHAs), hydrogels or other self-assembling materials such as peptide based nanostructured fibrous scaffolds.

The stem or progenitor cells may be encapsulated using substances such as alginate (Tsang et al., 2007). Additionally, encapsulation embodies macroencapsulation made by substances including chitosan, polyethylene glycol (PEG), poly-L-lysine (PLL), poly-L-ornithine14, poly(methylene-co-guanidine) hydrochloride, pluronics, glycerol phosphate, hyaluronic acid, cellulose phosphate, starch, agarose, carrageenan, silk fibroin, gelatine and gellan gum. These cell-encapsulation combinations may promote better survival of frozen cells and ensure temporary or permanent physical isolation of the stem or progenitor cells and avoid any potential immune rejection of the cells following transplantation.

The compositions of the present invention are suitable for use in therapy, including the treatment of: (i) neurological diseases, including chronic stroke disability, acute stroke, traumatic brain injury, Alzheimer's disease, Parkinson's disease, Huntington's disease, amyotrophic lateral sclerosis and related diseases; (ii) diseases of the vasculature, including peripheral ischemia, peripheral arterial disease, myocardial infarction, diabetes induced vascular disease and related diseases; (iii) diseases of the retina, including retinitis pigmentosa, age-related macular degeneration, diabetic retinopathy and related diseases; (iv) autoimmune diseases including Crohn's disease, rheumatoid arthritis, diabetes mellitus type 1 and related diseases; and (v) haematological cancers including leukaemias, lymphomas, myelomas and related diseases.

Cells formulated according to the present invention do not need to be further processed to remove DMSO or other toxic compounds from the storage or preparation medium, as the product is compatible with cell delivery devices and is not toxic by clinical administration.

The invention will now be described by reference to the following non-limiting example.

Method

Formulation of Neural Stem Cells, Retinal Progenitor Cells and Mesenchymal Stem Cells Neural stem cells were derived from human foetal brain and maintained in tissue culture as described by Pollock et al (2006). Retinal progenitor cell cultures were obtained from foetal retina and maintained in tissue culture as described by Aftab et al (2009). Human mesenchymal stem cells isolated from bone marrow withdrawn from the posterior iliac crest of the pelvic bone of normal volunteers, were obtained from Lonza (Catalogue number: PT-2501) and cultured as recommended by the manufacture using their proprietary media MSCGM (Mesenchymal Growth Media). Cells supplied at passage 2 were cultured over 3 passages using a trypsin/EDTA and initial seeding densities between 5000-6000 cells per $cm^2$ prior to formulation as described below.

Cultures of cells were expanded in T-flasks until 70 to 90% confluent. The spent medium was aspirated and then the cell monolayer washed with HBSS without magnesium or calcium ions (Invitrogen). The wash was aspirated and then the cells dissociated with recombinant bovine trypsin (Lonza TrypZean/EDTA) for 5 minutes at 37° C. The dissociated cell suspension was mixed with a trypsin inhibitor solution (0.55 mg/ml soybean trypsin inhibitor [Sigma], 1% HSA [Grifols], 25 U/ml benzon nuclease [VWR] in DMEM:F12 [Invitrogen]) and centrifuged for 5 minutes at ~500×g. The supernatant was aspirated and the cell pellet washed in 50% Hypo-Thermosol®-FRS (BioLife Solutions, Inc) in DMEM:F12 followed by centrifugation at ~500×g for 5 minutes. The cell pellet was then suspended in HypoThermosol®-FRS at a concentration of 40,000 to 60,000 cells/µl.

Cells were also thawed from cryopreservation medium (culture medium supplemented with 10% DMSO [WAK-Chemie Medical]) in a bath of 37° C. water for 2 minutes, then washed and formulated in HypoThermosol®-FRS as above.

Control samples formulated in saline containing Trolox were washed in DMEM:F12 instead of 50% HypoThermosol®-FRS in DMEM:F12, then suspended in HBSS without magnesium or calcium ions supplemented with 0.5 mM n-acetyl cysteine and 0.5 to 1 µM Trolox (Sigma).

Control samples formulated in saline were washed in DMEM:F12 instead of 50% HypoThermosol®-FRS in DMEM:F12, then suspended in HBSS without magnesium or calcium ions supplemented with 0.5 mM n-acetyl cysteine (Sigma).

Comparison of Cells Formulated in HypoThermosol®-FRS and Saline

Figure 1:
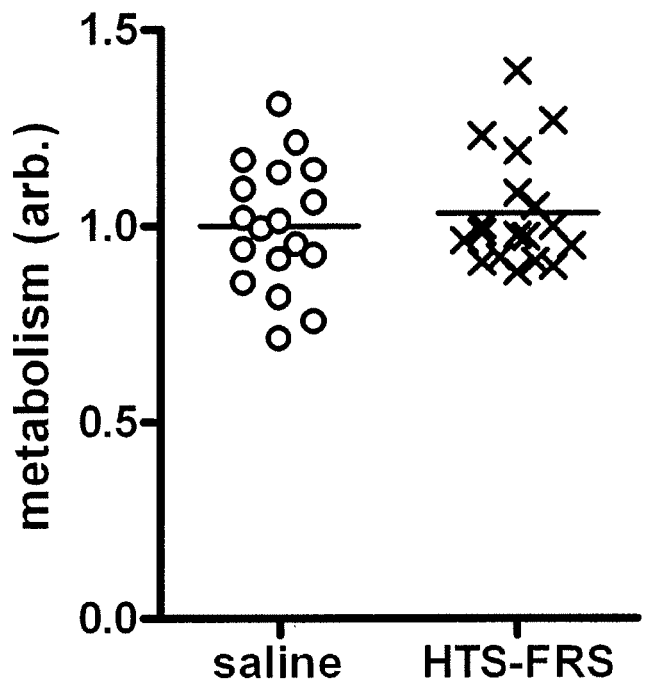
FIG. 1 is a graph showing that the metabolic activity of neural stem cells formulated in HypoThermosol®-FRS is comparable with that of stem cells formulated in saline.

The metabolic activity of neural stem cells formulated in HypoThermosol®-FRS is comparable with those formulated in saline solution. Formulations of cells in HypoThermosol®-FRS or saline were stored for 1 hour then subjected to a metabolic activity assay (Dojindo CCK-8) over 1 hour in culture. The result was normalized to take into account the number of the cells present by using a cell quantification assay (Invitrogen CyQUANT). The data show that cells formulated in HypoThermosol®-FRS have a comparable metabolic activity as those formulated in saline (see FIG. 1).

As shown in Table 1, saline and HTS-FRS formulated neural cells give rise to cultures with comparable immunoreactivity to phenotype markers. Formulations of cells in Hypo-Thermosol®-FRS or saline were stored for up to 8 hours. The nestin immunoreactivity of the formulations was then measured using a fluorescent antibody and flow cytometry, and immunoreactivity remained above a predetermined 93% lower limit (saline=99.9%; HypoThermosol®-FRS=99.8%). Samples of the formulated cells were then suspended in expansion culture medium and seeded onto laminin coated tissue culture dishes. Both cultures produced adherent, healthy cells with normal appearance. These cells were then analyzed by immunocytochemistry and measured to be above a predetermined limit of 95% nestin immunoreactive. Upon withdrawal of mitogens for 7 days the stem cells differentiated into neural phenotypes with immunoreactivity to phenotype markers within predetermined limits (marker specificities: GFAP=astrocytes; GalC=oligodendrocytes; DCX and TUBB3=neurons).

TABLE 1

|  | Predetermined limits | Saline | HTS-FRS | Result |
|---|---|---|---|---|
| Undifferentiated | nestin ≥95% | 99.7% | 99.5% | pass |
| 7 d withdrawal | GFAP 6.2%-25.8% | 18.4% | 10.2% | pass |
| from mitogens | GalC 8.3%-36.0% | 28.2% | 12.2% | pass |
|  | DCX 3.6%-29.3% | 9.0% | 13.1% | pass |
|  | TUBB3 83.8%-100% | 99.3% | 99.4% | pass |

Hypothermic Storage

Figure 2:
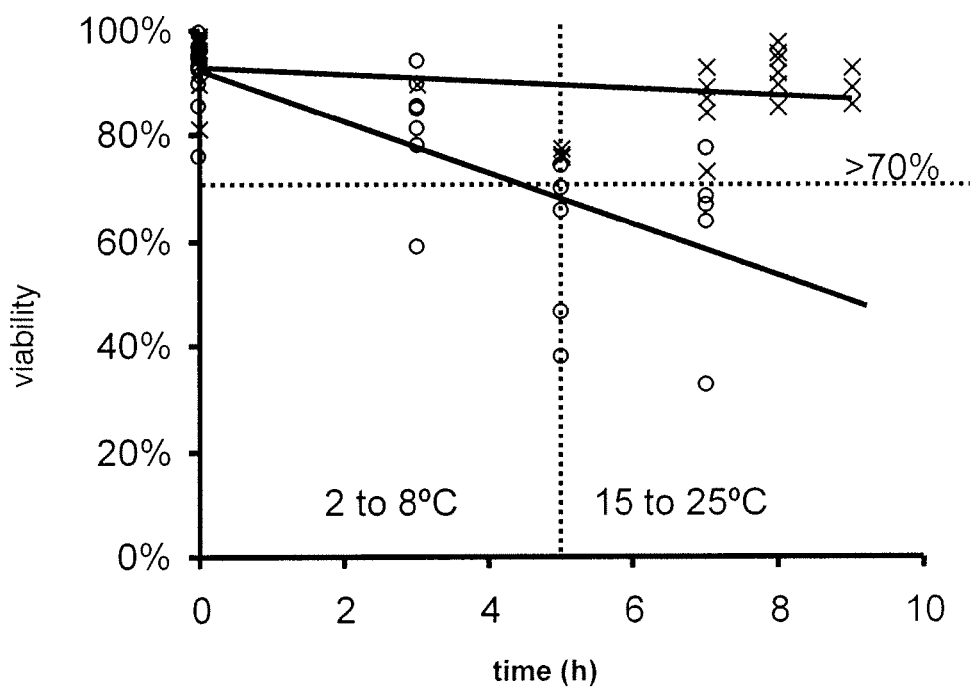
FIG. 2 is a graph showing exemplar neural stem cell viability during shelf-life studies of 5 hours at 2° C. to 8° C. followed by thawing at ambient temperature for up to 4 hours.

Shelf-life studies have assessed the viability of the therapeutic and commercially manufactured neural stem cell line, CTX0E03 (Pollock et al., 2006), formulated in saline or using the method described in this invention using HTS-FRS. In general, the cells will be stored at 2° C. to 8° C. prior to administration. However, the storage conditions of the cells will be at ambient temperature during administration, and this temperature shift has been taken into account during the shelf-life assays. The data from all experiments employing 5 hour storage at 2° C. to 8° C. followed by a temperature shift to ambient are presented in FIG. 2, which clearly demonstrates the increase in viable shelf-life afforded by HTS-FRS over saline formulations. Where there has been a process comparison with cells from the same culture, the average increase in viability at 7 hours accorded by the HTS-FRS process over the HBSS+NAC process is 22.7% (mean HBSS+NAC viability=58.9%; mean HTS-FRS viability=81.6%). On every occasion to date, the viability of the HTS-FRS formulation of the present invention has remained above the >70% acceptance criterion, as set by regulatory authorities for viable cell products.

Figure 3:
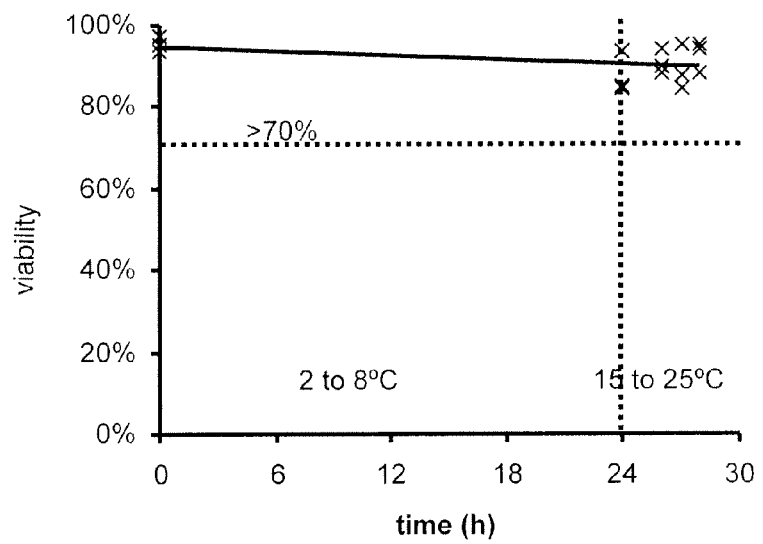
FIG. 3 is a graph showing overnight storage of exemplar neural stem cells in HTS-FRS for 24 hours at 2° C. to 8° C. followed by 4 hours at ambient temperature.
Figure 4:
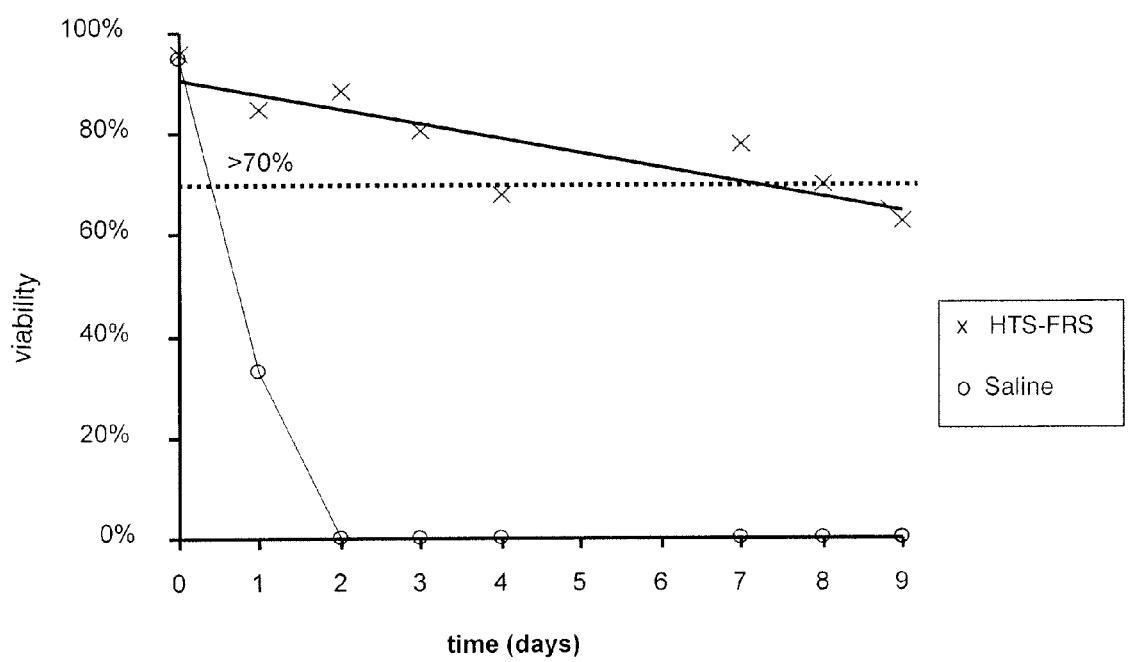
FIG. 4 is a graph showing exemplar neural stem cell viability during shelf-life studies of 9 days at 2° C. to 8° C.
Figure 5:
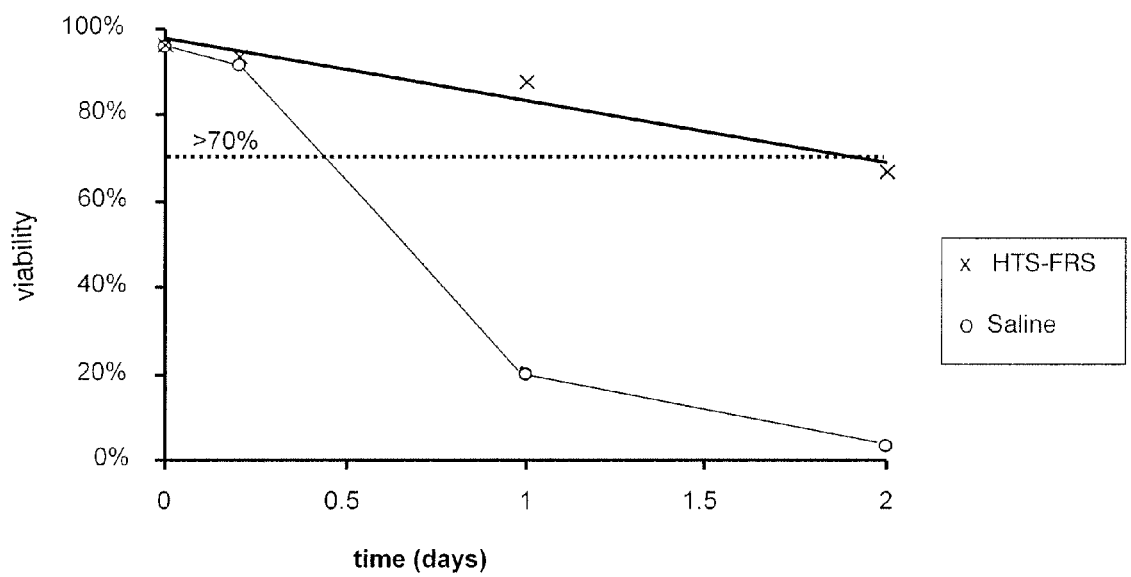
FIG. 5 is a graph showing exemplar neural stem cell viability during shelf-life studies of 2 days at ambient temperature.

In addition, the overnight hypothermic storage of CTX0E03 cells has been demonstrated. Independent cell formulations remained viable for 24 hours at 2° C. to 8° C. and following an additional 4 hours at ambient temperature to mimic clinical administration temperatures (see FIG. 3). Furthermore, cells formulated in HTS-FRS remain viable at 2° C. to 8° C. for up to 7 days, where saline formulated cells are non-viable within 2 days (See FIG. 4). Part of the cell-preserving properties of HTS-FRS can be attributed to the vitamin E derivative, Trolox, which can preserve neural stem cells for 2 days in saline solution at ambient temperature (See FIG. 5). These data show successful short-term and medium-term storage of cell therapies in hypothermic conditions following the method of this invention.

Figure 6:
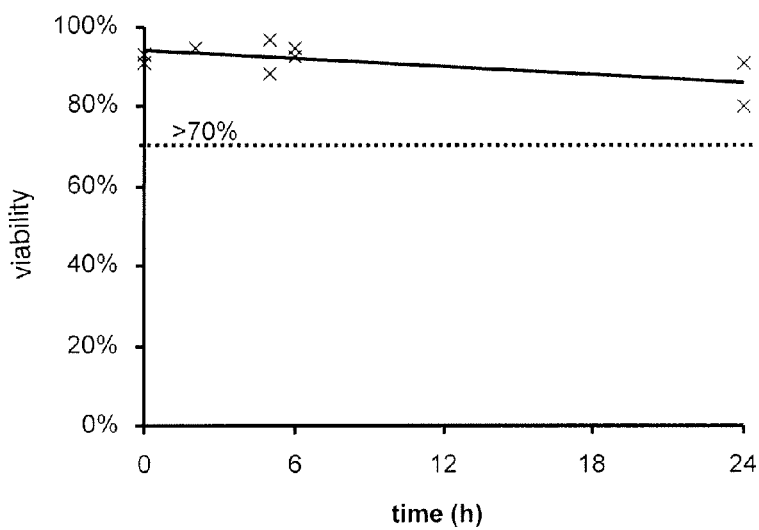
FIG. 6 is a graph showing retinal progenitor cell viability during shelf-life studies of 24 hours at 2° C. to 8° C. wherein thawed cryopreserved cells were formulated in HTS-FRS without an intermediate culture step.
Figure 7:
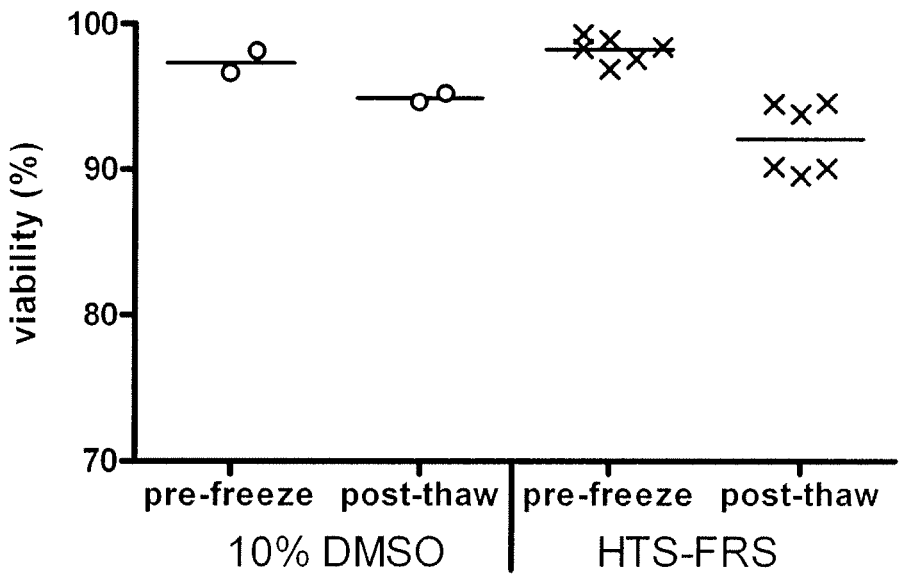
FIG. 7 is a graph showing cryopreservation of exemplar neural stem cells for 4 days at −80° C. in media containing either 10% DMSO or HTS-FRS.

FIG. 6 shows retinal progenitor cell viability during shelf-life studies of 24 hours at hypothermic temperatures. Thawed cryopreserved cells were formulated in HTS-FRS without an immediate culture step.

Cryothermic Storage

Figure 8:
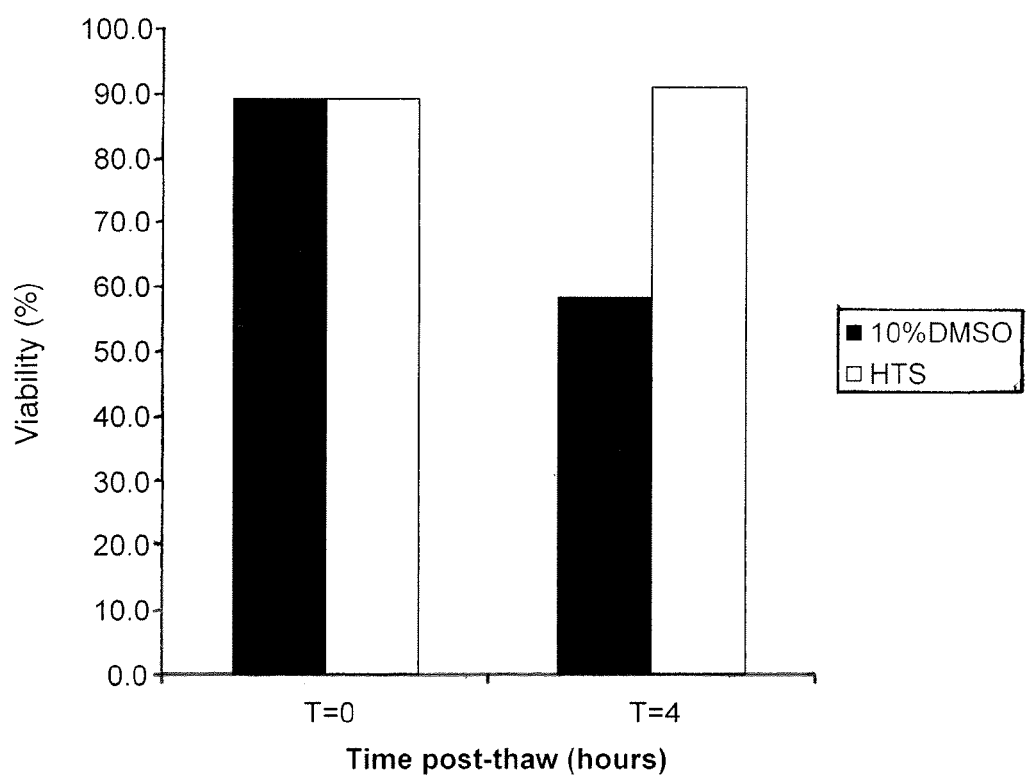
FIG. 8 is a graph showing the viability of exemplar neural stem cells immediately upon thawing and 4 hours post-thaw at ambient temperature, wherein cells were cryopreserved for one month in liquid nitrogen vapour in media containing either 10% DMSO or HTS-FRS.

Cryopreservation of neural stem cells, retinal progenitor cells and mesenchymal stem cells has been successfully achieved using the method of the present invention. Cells can be formulated according to the method of the invention and stored at −80° C. for up to 4 days, with no deterioration in cell viability (See FIGS. 7-10). The HTS-FRS non-toxic solution was as effective in maintaining the viability of the cells following cryopreservation as was achieved using current methods that incorporate 10% DMSO (See FIGS. 8-10). Additionally, the thawed cells of the invention have been shown to maintain their viability following defrosting in HTS-FRS (See FIGS. 8-10). Furthermore, these thawed cells have been shown to plate in tissue culture with the same biological activity as cells cryopreserved using 10% DMSO.

Device Compatibility

One of the key attributes of an acceptable excipient for administration of a cell therapy product is its compatibility with the surgical apparatus with which it will be delivered in the clinic. The differences in viscosity and density of a cell therapy formulated according to the method described herein and saline solution could theoretically impact upon the ability of the vehicle to carry the cells through the syringe and cell delivery cannula. However, as shown in Table 2, cells formulated in HypoThermosol®-FRS pass through a cell delivery cannula with the same success as those formulated in saline. The cell formulation (50,000 cells/µl) was drawn into a 250 µl glass syringe, and 200 µl was ejected through a 19 cm cell delivery cannula at a rate of either 1 or 5 µl/min. The viability of the cells was assessed by trypan blue exclusion, and the concentration of the cells measured using a haemocytometer. Additionally, the nestin immunoreactivity of the cells was measured using a fluorescent antibody and flow cytometry. Viability was acceptable for each formulation. The cell concentration remained constant. The nestin immunoreactivity remained above a predetermined 93% lower limit. These results further substantiate the use of HTS-FRS as an excipient.

TABLE 2

| Ejection rate | Pass/fail criteria | Saline | HTS-FRS | Result |
|---|---|---|---|---|
| 5 µl/min | ≥70% viable | 96.4% viable | 94.7% viable | pass |
|  | 40,000 to 60,000 cells/µl | 51,156 cells/µl | 51,778 cells/µl | pass |
|  | ≥93.0% nestin+ | 96.6% nestin+ | 99.0% nestin+ | pass |
| 1 µl/min | ≥70% viable | 94.1% viable | 93.9% viable | pass |
|  | 40,000 to 60,000 cells/µl | 51,000 cells/µl | 50,689 cells/µl | pass |
|  | ≥93.0% nestin+ | 97.6% nestin+ | 99.2% nestin+ | pass |

Cell Viability and Concentration Assay

Samples of cells were mixed 1:1 with 0.4% Trypan blue (Sigma) and loaded onto a haemocytometer. Viable cells exclude the dye from the cytoplasm and are colourless. Non-viable cells which have lost their plasma-membrane integrity stain blue. The viability and concentration of the sample is determined by counting the cells within a grid of the haemocytometer using 10× objective phase-contrast microscopy.

The formulation of human stem cells and progenitor cells according to the present invention prolongs the viable shelf life of the product from the previous standard of approximately 3 hours to at least 24 hours when stored at 2° C. to 8° C. In addition, cells can tolerate cryopreservation in this same storage medium, at temperatures of less than −70° C. for greater than 4 days and in liquid nitrogen storage conditions (~−195° C.) for at least 6 months. These improvements in shelf-life do not impact upon the characteristics of the stored product, allowing unimpinged potency.

Toxicity

The toxicity of cell therapies formulated according to the method in this invention will not be altered. When implanted into mice there was no overt toxicity associated either with the HypoThermosol®-FRS vehicle or in combination with neural stem cells. These studies have included intracranial and intramuscular administration. In addition, a toxicity study has been completed in rats, showing no difference between the response of the subject to intracranial administration of HypoThermosol®-FRS or saline solution, and no overt reaction to either solution.

The content of all publications described herein is incorporated herein by reference.

REFERENCES

Aftab U, Jiang C, Tucker B, Kim J-Y, Klassen H, Miljan E, Sinden J, Young M (2009) Growth kinetics and transplantation of human retinal progenitor cells. Experimental Eye Research 89; 301-310.

Bible E, Chau, Y S, Alexander M R, Price J, Shakesheff K R, Modo M. (2009) The support of neural stem cells transplanted into stroke-induced brain cavities by PLGA particles. Biomaterials 30: 2985-2994.

Calmels B, Houze P, Hengesse J C, Ducrot T, Malenfant C, Chabannon C (2003) Preclinical evaluation of an automated closed fluid management device: Cytomate, for washing out DMSO from hematopoietic stem cell grafts after thawing. Bone Marrow Transplant 31:823-828.

Hubel A (2001) Cryopreservation of HPCs for clinical use. Transfusion 41:579-580.

Ikonomovic M, Kelly K M, Hentosz T M, Shih S R, Armstrong D M, Taylor M J (2001) Ultraprofound cerebral hypothermia and blood substitution with an acellular synthetic solution maintains neuronal viability in rat hippocampus. Cryo Letters 22:19-26.

Pollock K, Stroemer P, Patel, Stevanato L, Hope A, Miljan E, Dong Z, Hodges H, Price J, Sinden J D (2006) A conditionally immortal clonal stem cell line from human cortical neuroepithelium for the treatment of ischemic stroke. Exp Neurol. 199(1):143-55.

Sauer-Heilborn A, Kadidlo D, McCullough J (2004) Patient care during infusion of hematopoietic progenitor cells. Transfusion 44:907-916.

Storey B T, Noiles E E, Thompson K A (1998) Comparison of glycerol, other polyols, trehalose, and raffinose to provide a defined cryoprotectant medium for mouse sperm cryopreservation. Cryobiology 37:46-58.

Syme R, Bewick M, Stewart D, Porter K, Chadderton T, Gluck S (2004) The role of depletion of dimethyl sulfoxide before autografting: on hematologic recovery, side effects, and toxicity. Biol Blood Marrow Transplant 10:135-141.

Taylor M J, Bailes J E, Elrifai A M, Shih S R, Teeple E, Leavitt M L, Baust J G, Maroon J C (1995) A new solution for life without blood. Asanguineous low-flow perfusion of a whole-body perfusate during 3 hours of cardiac arrest and profound hypothermia. Circulation 91:431-444.

Tsang, Wen-Ghih; Zheng, Tianli; Wang, Yanping; Tang, Jinghua; Rind, Howard B.; Francki, Aleksander; Bufius, Nataliya (2007) Generation of Functional Islet-Like Clusters After Monolayer Culture and Intracapsular Aggregation of Adult Human Pancreatic Islet Tissue. Transplantation 83(6):685-693.

Williams S K, Senechal G (2001) Safety of Hypothermosol for Intra-Cardiac Injection. In. Tuscon, Ariz., USA: University of Arizona Health Sciences Center.

The invention claimed is:

1. A method of formulating human neural stem cells, mesenchymal stem cells, or retinal progenitor cells for direct administration to a patient, comprising:
   (i) suspending the cells in a composition comprising:
      Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine and glutathione, wherein the composition does not include a dipolar aprotic solvent,
   (ii) storing the cell suspension at a cryothermic temperature; and
   (iii) thawing the stored suspension,
   wherein at least 70% of the cells are viable after thawing.

2. The method according to claim 1, wherein the cells are recovered from a cell-culture system.

3. The method according to claim 1, wherein said storing is carried out at a temperature of −70° C. to −200° C.

4. The method according to claim 1, wherein the cell suspension is stored at a hypothermic temperature after said storing or said thawing.

5. The method according to claim 4, wherein the hypothermic storage is carried out at a temperature of 2° C. to 8° C.

6. The method according to claim 1, wherein the cells are mesenchymal stem cells.

7. The method according to claim 1, wherein the cells are neural stem cells.

8. The method according to claim 1, wherein the cells are retinal progenitor cells.

9. The method according to claim 1, wherein the cells are comprised in a polymeric scaffold or micro-carrier.

10. The method according to claim 9, wherein the polymeric scaffold or microcarrier is PLGA.

11. The method according to claim 1, wherein the cells are encapsulated.

12. The method according to claim 11, wherein the cells are encapsulated in a substance selected from alginate, chitosan, PEG, PLL, poly-L-ornithine14, poly(methylene-co-guanidine) hydrochloride, pluronics, glycerol phosphate, hyaluronic acid, cellulose phosphate, starch, agarose, carrageenan, silk fibroin, gelatine and gellan gum.

13. The method according to claim 1, further comprising loading the suspended cells into a cell delivery cannula.

14. A method for delivery of human neural stem cells, mesenchymal stem cells, or retinal progenitor cells, comprising:
   thawing a composition stored at a cryothermic or hypothermic temperature, wherein the composition comprises the neural stem cells, mesenchymal stem cells, or retinal progenitor cells, Trolox, $Na^+$, $K^+$, $Ca^{2+}$, $Mg^{2+}$, $Cl^-$, $H_2PO_4^-$, HEPES, lactobionate, sucrose, mannitol, glucose, dextran-40, adenosine and glutathione, wherein the composition does not include a dipolar aprotic solvent; and
   directly administering the composition to a patient in need thereof, wherein the method includes no rinsing of the composition after said thawing and before said administering, wherein the cells of the administered composition are viable and differentiate in vivo, and wherein at least 70% of the cells are viable after thawing.

15. The method according to claim 14, wherein the composition is administered via implantation into tissue or systemic delivery.

16. The method according to claim 14, wherein the composition is administered to the patient via a cell delivery cannula.

* * * * *